(12) United States Patent
Harada et al.

(10) Patent No.: US 10,131,987 B2
(45) Date of Patent: Nov. 20, 2018

(54) RAW MATERIAL FOR CHEMICAL DEPOSITION INCLUDING ORGANORUTHENIUM COMPOUND, AND CHEMICAL DEPOSITION METHOD USING THE RAW MATERIAL FOR CHEMICAL DEPOSITION

(71) Applicant: TANAKA KIKINZOKU KOGYO K.K., Chiyoda-ku, Tokyo (JP)

(72) Inventors: Ryosuke Harada, Tsukuba (JP); Toshiyuki Shigetomi, Tsukuba (JP); Kazuharu Suzuki, Tsukuba (JP); Shunichi Nabeya, Tsukuba (JP); Takayuki Sone, Tsukuba (JP); Akiko Kumakura, Tsukuba (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 0 days.

(21) Appl. No.: 15/514,778

(22) PCT Filed: Sep. 24, 2015

(86) PCT No.: PCT/JP2015/076867
§ 371 (c)(1),
(2) Date: Mar. 27, 2017

(87) PCT Pub. No.: WO2016/052288
PCT Pub. Date: Apr. 7, 2016

(65) Prior Publication Data
US 2017/0218509 A1    Aug. 3, 2017

(30) Foreign Application Priority Data
Oct. 3, 2014 (JP) .................... 2014-204505

(51) Int. Cl.
*C23C 16/18* (2006.01)
*C07F 15/00* (2006.01)
(Continued)

(52) U.S. Cl.
CPC .............. *C23C 16/18* (2013.01); *C07F 15/00* (2013.01); *C07F 15/0046* (2013.01);
(Continued)

(58) Field of Classification Search
CPC .................... H01L 21/02271; H01L 31/02966
See application file for complete search history.

(56) References Cited

U.S. PATENT DOCUMENTS 6,316,064 B1 * 11/2001 Onozawa ................ C23C 16/18
427/250

FOREIGN PATENT DOCUMENTS

JP    2007-526250 A    9/2007
JP    2008-69453 A     3/2008
(Continued)

OTHER PUBLICATIONS

PCT, International Search Report for PCT/JP2015/076867, dated Nov. 17, 2015.
(Continued)

*Primary Examiner* — Mohammad Choudhry
(74) *Attorney, Agent, or Firm* — Orrick, Herrington & Sutcliffe LLP; Joseph A. Calvaruso

(57) ABSTRACT

The invention provides a raw material for chemical deposition having properties required for a CVD compound, that is, which has a high vapor pressure, can be formed into a film at low temperatures (about 250° C. or less), and also has moderate thermal stability. The invention relates to a raw material for chemical deposition, for producing a ruthenium thin film or a ruthenium compound thin film by a chemical
(Continued)

deposition method, the raw material for chemical deposition including an organoruthenium compound represented by the following formula, in which a cyclohexadienyl group or a derivative thereof and a pentadienyl group or a derivative thereof are coordinated to ruthenium:

[Chemical Formula 1]

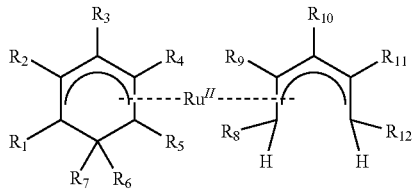

wherein the substituents $R_1$ to $R_{12}$ are each independently a hydrogen atom, a linear or cyclic hydrocarbon, an amine, an imine, an ether, a ketone, or an ester, and the substituents $R_1$ to $R_{12}$ each have 6 or less carbon atoms.

2 Claims, 2 Drawing Sheets

(51) Int. Cl.
 *H01L 21/28* (2006.01)
 *H01L 21/285* (2006.01)
 *C07F 17/02* (2006.01)
 *C09D 1/00* (2006.01)

(52) U.S. Cl.
 CPC ............ *C07F 17/02* (2013.01); *C09D 1/00* (2013.01); *H01L 21/28* (2013.01); *H01L 21/285* (2013.01); *H01L 21/28506* (2013.01)

(56) References Cited

FOREIGN PATENT DOCUMENTS

| JP | 2010-513467 A | 4/2010 |
| JP | 2012-92025 A | 5/2012 |
| WO | WO 2014/088108 A1 | 6/2014 |

OTHER PUBLICATIONS

Kawano et al., Ligand Structure Effect on a Divalent Ruthenium Precursor for MOCVD, Mater. Res. Soc. Symp. Proc. vol. 1155, pp. 35-40, 2009 Materials Research Society.
EP, Extended Search Report for EP application No. 15745773.9, dated May 15, 2018.
Gregorczyk et al.,"Atomic Layer Deposition of Ruthenium Using the Novel Precursor bis(2,6,6-trimethyl-cyclohexadienyl)ruthenium", Chemistry of Materials, vol. 23, No. 10, May 24, 2011, pp. 2650-2656, XP055473005, ISSN: 0897-4756.

* cited by examiner

TEST No. 3  TEST No. 4  TEST No. 5

RAW MATERIAL FOR CHEMICAL DEPOSITION INCLUDING ORGANORUTHENIUM COMPOUND, AND CHEMICAL DEPOSITION METHOD USING THE RAW MATERIAL FOR CHEMICAL DEPOSITION

TECHNICAL FIELD

The present invention relates to a raw material for chemical deposition including an organoruthenium compound for producing a ruthenium thin film or a ruthenium compound thin film by a chemical deposition method (chemical vapor deposition method (CVD) and atomic layer deposition method (ALD)). Specifically, it relates to a raw material for chemical deposition having a low decomposition temperature and also having moderate thermal stability.

BACKGROUND ART

As thin-film electrode materials for semiconductor devices, such as DRAM and FERAM, ruthenium and ruthenium compounds are used. As a method for producing of such a thin film, a chemical deposition method, such as CVD (chemical vapor deposition method) or ALD (atomic layer deposition method), is applied. As raw material compounds for use in such a chemical deposition method, a large number of organoruthenium compounds are conventionally known.

Generally, as a required property of an organoruthenium compound for chemical deposition, to efficiently form a thin film, a high vapor pressure is required. Additionally, considering handleability, it is preferable that the compound is in a liquid state at ambient temperature. From such a point of view, cyclic or linear dienyl-coordinated organoruthenium compounds are used. Many of cyclic or linear dienyl-coordinated compounds have relatively high stability in air and are easy to handle.

Examples of compounds having a cyclopentadienyl group include bis(ethylcyclopentadienyl)ruthenium $Ru(EtCp)_2$ and (2,4-dimethylpentadienyl)(ethylcyclopentadienyl)ruthenium $Ru(EtCp)(Me_2PD)$ represented by the following formulae (Non Patent Document 1). Examples of compounds in which two pentadienyl groups are coordinated include bis(2,4-dimethylpentadienyl)ruthenium $Ru(Me_2PD)_2$ and bis(1-ethylpentadienyl)ruthenium $Ru(EtPD)_2$ (Non Patent Document 1, Patent Document 1), and, as a compound in which a cyclohexadienyl group is coordinated, bis(2,6,6-trimethylcyclohexadienyl)ruthenium $Ru(Me_3CHD)_2$ can be mentioned (Patent Document 2).

[Chemical Formula 1]

In the above formulae, EtCp is ethylcyclopentadienyl,
$Me_2PD$ is 2,4-dimethylpentadienyl,
EtPD is 1-ethylpentadienyl, and
$Me_3CHD$ is 2,6,6-trimethylcyclohexadienyl.

The above compounds have relatively high vapor pressures, and many are liquids at ambient temperature. In particular, when attention is paid to the decomposition temperature, the decomposition temperatures of $Ru(EtCp)(Me_2PD)$ and $Ru(Me_2PD)_2$ are as low as about 270° C. and about 210° C., respectively, and thus these compounds can be easily formed into films even at low temperatures.

RELATED ART DOCUMENT

Patent Documents

Patent Document 1: JP 2008-69453 A
Patent Document 2: JP 2010-513467 A

Non Patent Document

Non Patent Document 1: Materials Research Society Symposium Proceedings 1155-C09-11 (2009).

SUMMARY OF THE INVENTION

Problems to be Solved by the Invention

Here, when a ruthenium thin film or a ruthenium compound thin film is formed on a semiconductor device or the like, sometimes high-temperature conditions cannot be applied. Thus, there is a demand to provide an organoruthenium compound that can be formed into a film at a temperature as low as possible. Accordingly, a compound that can be formed into a film at a temperature lower than the decomposition temperature 270° C. of $Ru(EtCp)(Me_2PD)$ (e.g., around 250° C.) is preferable. Meanwhile, when only the decomposition temperature is taken into consideration, the decomposition temperature of $Ru(Me_2PD)_2$ is as low as 210° C. However, because of the extremely low decomposition temperature, $Ru(Me_2PD)_2$ has low thermal stability and is difficult to handle. For example, because the sample heating temperature is made low (about 80° C. or less) to prevent pyrolysis at the time of film formation, the vapor pressure decreases at the time of film formation.

Against this background, the present invention provides a raw material for chemical deposition having properties required for a CVD compound, that is, which has a high vapor pressure, can be formed into a film at low temperatures (about 250° C. or less), and also has moderate thermal stability.

Means for Solving the Problems

The present invention for solving the problem relates to a raw material for chemical deposition, for producing a ruthenium thin film or a ruthenium compound thin film by a chemical deposition method, the raw material for chemical deposition including an organoruthenium compound represented by the following formula, in which a cyclohexadienyl group or a derivative thereof and a pentadienyl group or a derivative thereof are coordinated to ruthenium:

[Chemical Formula 2]

wherein the substituents $R_1$ to $R_{12}$ are each independently a hydrogen atom, a linear or cyclic hydrocarbon, an amine, an imine, an ether, a ketone, or an ester, and the substituents $R_1$ to $R_{12}$ each have 6 or less carbon atoms.

The raw material for chemical deposition of the present invention includes an organoruthenium compound having a pentadienyl group and also a cyclohexadienyl group as ligands. The compound has a low decomposition temperature (around 250° C.) and can be formed into a film at low temperatures, and also has moderate thermal stability and thus has excellent handleability.

As described above, the raw material for chemical deposition of the present invention is characterized by having both a cyclohexadienyl group ligand and a pentadienyl group ligand. In this regard, the present inventors have noted that depending on the kind, ligands for ruthenium have the following tendencies in terms of the strength of bonding between the ligand and ruthenium and the thermal stability of the compound.

Strength of Bonding Between Ligand and Ru

Ru-cyclopentadienyl>Ru-cyclohexadienyl>Ru-pentadienyl (linear dienyl)

Then, the present inventors have found that when a compound has both a cyclohexadienyl group ligand and a pentadienyl group ligand with ruthenium, the resulting compound has moderate thermal properties as follows, and thus arrived at the present invention described above.

Thermal Stability of Compound

Ru(EtCp)$_2$ (decomposition temperature: 350° C.)>Ru(Me$_3$CHD)$_2$>Ru(EtCp)(Me$_2$PD) (decomposition temperature: 270° C.)>the compound of the present invention>Ru(Me$_2$PD)$_2$ (decomposition temperature: 210° C.)

Hereinafter, each component of the raw material for chemical deposition of the present invention will be described in detail.

The "cyclohexadienyl group or derivative thereof" has substituents $R_1$ to $R_7$. The substituents $R_1$ to $R_7$ are each a hydrogen atom, a linear or cyclic hydrocarbon, an amine, an imine, an ether, a ketone, or an ester. Preferably, the substituents $R_1$ to $R_7$ are each a hydrogen atom or a $C_{1-6}$ linear or branched hydrocarbon. As a hydrocarbon, a methyl group or an ethyl group is preferable. The substituents $R_1$ to $R_7$ each have six or less, preferably three or less, and particularly preferably two or less carbon atoms. Further, preferably, out of the substituents $R_1$ to $R_7$, two to four substituents are each a hydrogen atom, and the remaining substituents are each a methyl group or an ethyl group, and it is preferable that the substituents $R_6$ and $R_7$ are each a methyl group or an ethyl group. When the number of alkyl substituents is too large relative to hydrogen atoms, or the carbon chains of the alkyl substituents are too long, the vapor pressure decreases, and such a compound is undesirable as a raw material for chemical deposition.

The "pentadienyl group or derivative thereof" has substituents $R_8$ to $R_{12}$. The substituents $R_8$ to $R_{12}$ are each a hydrogen atom, a linear or cyclic hydrocarbon, an amine, an imine, an ether, a ketone, or an ester. Preferably, the substituents $R_8$ to $R_{12}$ are each a hydrogen atom or a $C_{1-6}$ linear or branched hydrocarbon. As a hydrocarbon, a methyl group or an ethyl group is preferable. In particular, preferably, out of the substituents $R_8$ to $R_{12}$, $R_8$, $R_{10}$, and $R_{12}$ are each a hydrogen atom, and the remaining substituents $R_9$ and $R_{11}$ are each a methyl group, an ethyl group, or a hydrogen atom. The substituents $R_8$ to $R_{12}$ each have six or less, preferably three or less, and particularly preferably two or less carbon atoms. When the number of alkyl substituents is too large relative to hydrogen atoms, or the carbon chains of the alkyl substituents are too long, the vapor pressure decreases, and thus such a compound is undesirable as a raw material for chemical deposition.

Additionally, as the pentadienyl group or derivative thereof, dimethylpentadienyl having two methyl groups as substituents is preferable. In particular, 2,4-dimethylpentadienyl wherein the substituents $R_9$ and $R_{11}$ are each a methyl group is preferable.

Specific examples of organoruthenium compounds include compounds of the following formulae. These compounds have decomposition temperatures of around 250° C. and can be easily formed into films at low temperatures.

[Chemical Formula 3]

[Chemical Formula 4]

[Chemical Formula 5]

The raw material for chemical deposition according to the present invention is useful for the formation of a ruthenium thin film by a chemical deposition method. In a chemical deposition method, an organoruthenium compound to serve as a raw material is heated and vaporized in a vacuum to produce a raw material gas. The raw material gas is blown to the heated substrate surface to pyrolyze the complex, thereby forming a ruthenium thin film. In such a method, the raw material described above is used as the organoruthenium compound.

The substrate heating temperature at the time of film formation may be 150° C. to 500° C. Because to achieve the substrate heating temperature on the low-temperature side is one of the objects of the present invention, the substrate heating temperature is preferably 150° C. to 400° C., more preferably 220° C. to 350° C. When the temperature is less than 150° C., the film forming reaction is difficult to proceed, making it difficult to obtain a necessary thickness. When the temperature is too high, it is difficult to form a uniform thin film, and, in the formation of a ruthenium film, the film is likely to be contaminated with impurities.

Advantageous Effects of the Invention

The raw material for chemical deposition of the present invention has a high vapor pressure, moderate thermal stability, and also a low decomposition temperature (about 250° C. or less), offering excellent film formability at low temperatures.

DESCRIPTION OF EMBODIMENTS

Hereinafter, best modes for carrying out the present invention will be described.

In this embodiment, three kinds of organoruthenium compounds represented by the following formulae were produced. Additionally, the decomposition temperature and the performance of the formed thin film were evaluated.

Synthesis of Compound A

As compound A, (2,4-dimethylpentadienyl)(2,6,6-trimethylcyclohexadienyl)ruthenium(II) was synthesized by the following steps.

2.38 ml of acetonitrile, 35.3 g (366.4 mmol) of 2,4-dimethyl 1,3-pentadiene, 13.5 g (183.2 mmol) of lithium carbonate, and 28.2 g (45.8 mmol) of di-μ-chlorodichlorobis[(1-3 η):(6-8 η)-2,7-dimethyloctadiendiyl]diruthenium (IV) were added to a flask containing 900 ml of ethanol in this order to form a suspension. The suspension was heated and stirred under reflux for 4 hours, and then cooled to room temperature. 5.6 g (45.8 mmol) of 2,6,6-trimethy-1,3-cyclohexadiene was added to the cooled liquid, and then heated and stirred under reflux for 6 hours. After the completion of the reaction, the mixture was cooled to room temperature and concentrated to give a muddy reaction mixture. Extraction from the muddy reaction mixture was performed with pentane, and the extract was subjected to column chromatography using a silica gel (or alumina) as the carrier and pentane as the eluent, and further to sublimation purification, thereby giving 2.0 g (6.3 mmol) of (2,4-dimethylpentadienyl)(2,6,6-trimethylcyclohexadienyl)ruthenium(II) as the object substance (yield: 7%, melting point: 104° C.).

[Chemical Formula 6]

Synthesis of Compound B

As compound B, (2,4-dimethylpentadienyl)(2,4,6,6-tetramethylcyclohexadienyl)ruthenium(II) was synthesized by the following steps.

1.04 ml of acetonitrile, 15.4 g (160 mmol) of 2,4-dimethyl 1,3-pentadiene, 6.0 g (80 mmol) of lithium carbonate, and 12.4 g (20 mmol) of di-µ-chlorodichloro-bis[(1-3 η):(6-8 η)-2,7-dimethyloctadiendiyl]diruthenium(IV) were added to a flask containing 400 ml of ethanol in this order to form a suspension. The suspension was heated and stirred under reflux for 4 hours, and then cooled to room temperature. 2.8 g (20 mmol) of 1,3,5,5-tetramethyl-1,3-cyclohexadiene was added to the cooled liquid, and then heated and stirred under reflux for 6 hours. After the completion of the reaction, the mixture was cooled to room temperature and concentrated to give a muddy reaction mixture. Extraction from the muddy reaction mixture was performed with pentane, and the extract was subjected to column chromatography using a silica gel (or alumina) as the carrier and pentane as the eluent, and further to sublimation purification, thereby giving 1.3 g (3.92 mmol) of (2,4-dimethylpentadienyl)(2,4,6,6-tetramethylcyclohexadienyl)ruthenium(II) as the object substance (yield: 10%, melting point: 67° C.).

[Chemical Formula 7]

Synthesis of Compound C (1)

As the compound C, (2,4-dimethylpentadienyl)(3-ethyl-2,6,6-trimethylcyclohexadienyl)ruthenium(II) was synthesized by the following steps.

0.52 ml of acetonitrile, 7.7 g (80 mmol) of 2,4-dimethyl 1,3-pentadiene, 3.0 g (40 mmol) of lithium carbonate, and 6.2 g (10 mmol) of di-µ-chlorodichloro-bis[(1-3 η):(6-8 η)-2,7-dimethyloctadiendiyl]diruthenium(IV) were added to a flask containing 200 ml of ethanol in this order to form a suspension. The suspension was heated and stirred under reflux for 4 hours, and then cooled to room temperature. 2.7 g (20 mmol) of 2-ethyl-1,5,5-trimethyl-1,3-cyclohexadiene was added to the cooled liquid, and then heated and stirred under reflux for 6 hours. After the completion of the reaction, the mixture was cooled to room temperature and concentrated to give a muddy reaction mixture. Extraction from the muddy reaction mixture was performed with pentane, and the extract was subjected to column chromatography using a silica gel (or alumina) as the carrier and pentane as the eluent, and further to distillation, thereby giving 0.8 g (3.92 mmol) of (2,4-dimethylpentadienyl)(3-ethyl-2,6,6-trimethylcyclohexadienyl)ruthenium(II) as the object substance (yield: 12%, melting point: −20° C. or less).

[Chemical Formula 8]

Synthesis of Compound C (2)

The synthesis of compound C was also performed by the following method.

114.4 g (1.19 mol) of 2,4-dimethyl 1,3-pentadiene and 31.1 g (0.21 mol) of 2-ethyl-1,5,5-trimethyl-1,3-cyclohexadiene were added to a flask containing 20.0 g (3.06 mol) of zinc in this order to form a suspension. A solution of 30.0 g (0.12 mol) of ruthenium chloride trihydrate dissolved in 500 ml of ethanol was slowly added dropwise to the suspension with stirring at room temperature. The mixture was stirred for about 30 minutes at room temperature, and then heated and stirred under reflux for 4 hours. After the completion of the reaction, the mixture was cooled to room temperature, and zinc was removed from the reaction solution by filtration, followed by concentration to give a reaction mixture.

Extraction from the obtained reaction mixture was performed with hexane, and the extract was subjected to column chromatography using a silica gel as the carrier and hexane as the eluent, and further to distillation, thereby giving 13.1 g (0.038 mol) of (2,4-dimethylpentadienyl)(3-ethyl-2,6,6-trimethylcyclohexadienyl)ruthenium(II) as the object substance (yield: 33%, melting point: −20° C. or less).

[Chemical Formula 9]

Incidentally, it was also possible to synthesize (2,4-dimethylpentadienyl)(2,6,6-trimethylcyclohexadienyl)ruthenium(II) and (2,4-dimethylpentadienyl) (2,4,6,6-tetramethylcyclohexadienyl)ruthenium(II) in the same manner as in the above Synthesis of Compound C (2).

The thermal properties of the compounds A, B, and C synthesized above were evaluated by DSC.

Calorimetry (DSC):

By use of Q2000 manufactured by TA Instruments, each compound (sample weight: 3.8 mg) was placed in a pressure-resistant cell made of stainless steel, and, in a nitrogen atmosphere, changes in heat were observed at a temperature rise rate of 10° C./min and a measurement temperature ranging from room temperature to 300° C. The results are shown in the following table. As the decomposition temperatures of the organoruthenium compounds (X1 to X3) of the following conventional examples, the values described in Non Patent Document 2 are also shown in the table.

Non Patent Document 2: Electrochemical and Solid-State Letters, Vol. 12, No. 10, pD80-83 (2009)

[Chemical Formula 10]

X1

X2

X3

TABLE 1

|  | Basic skeleton | Decomposition temperature |
| --- | --- | --- |
| Compound A | CHD—Ru—PD | 250° C. |
| Compound B | CHD—Ru—PD | 250° C. |
| Compound C | CHD—Ru—PD | 240° C. |
| Compound X1 | Cp—Ru—Cp | 350° C. |
| Compound X2 | Cp—Ru—PD | 270° C. |
| Compound X3 | PD—Ru—PD | 210° C. |

As shown by the above results, the decomposition temperatures of the compounds A to C were all 250° C. or less, allowing for film formation at low temperatures. At the same time, the decomposition temperatures were not low enough to cause decomposition during handling, and the compounds had moderate thermal stability.

Thermodravimetry-Differential Thermal Analysis (TG-DTA):

By use of TG-DTA2000SA manufactured by BRUKER, the compounds A, B, and C (sample weight: 5 mg) were each placed in a cell made of aluminum, and, in a nitrogen atmosphere, changes in heat and weight were observed at a temperature rise rate of 5° C./min and a measurement temperature ranging from room temperature to 500° C. The results are shown in FIG. 1.

Figure 1:
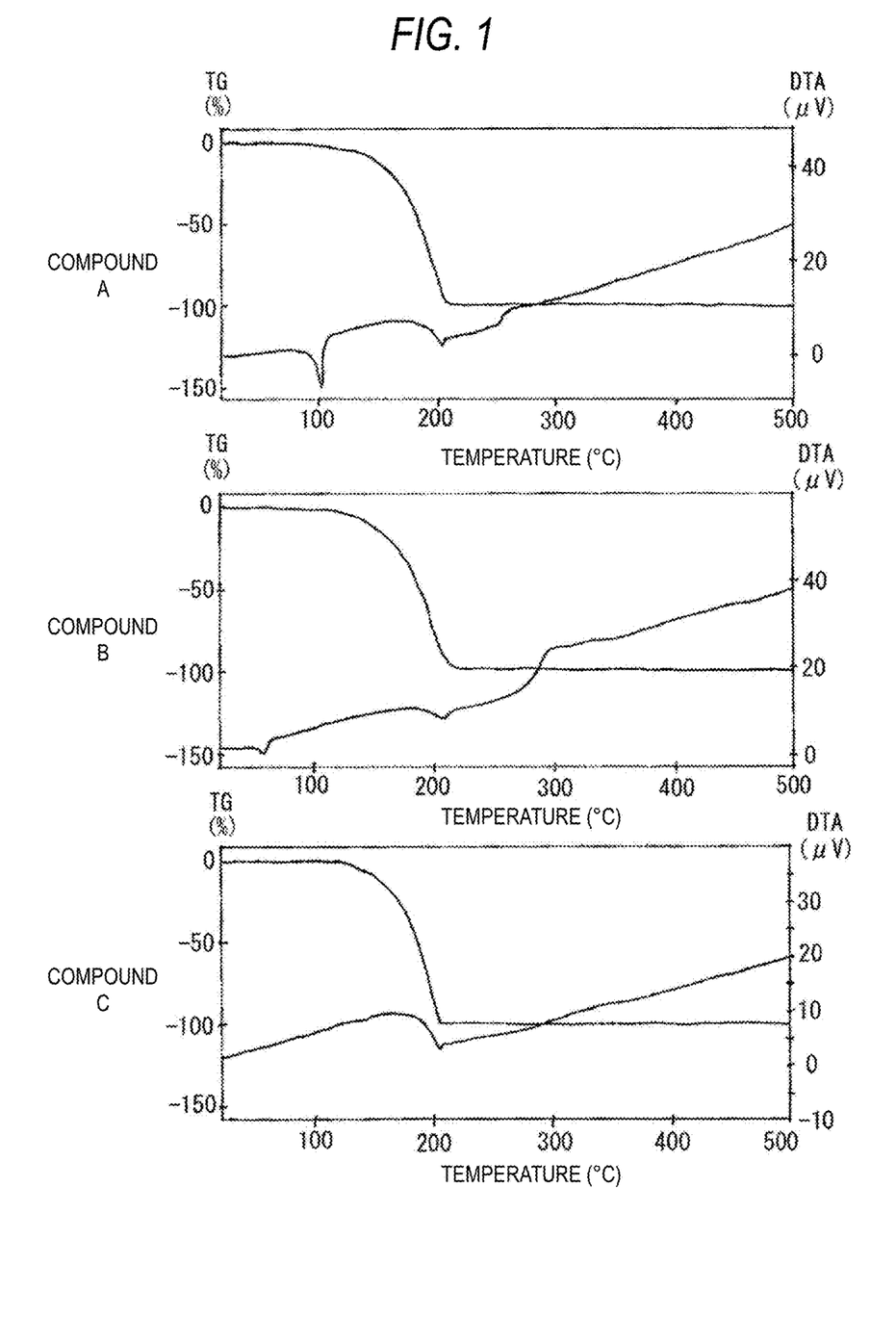
FIG. 1 is a diagram showing the results of the TG-DTA measurement of compounds in this embodiment.

From FIG. 1, in all the compounds A, B, and C, a weight loss was observed at 210° C. or less in TG, indicating that they are suitable for deposition at low temperatures (250° C. or less).

Deposition Test:

By use of a cold-wall film deposition device, ruthenium thin films were formed by CVD from the compound C as a raw material. In Test No. 1, the deposition conditions were as follows: substrate for thin film formation: silicon, sample heating temperature: 90° C., substrate heating temperature: 210° C., reactant gas: hydrogen supplied at 20 sccm, pressure: 150 torr, deposition time: 180 minutes. Additionally, films of Test Nos. 2 to 6 were also formed under the conditions shown in the following table, in which silicon oxide was used as the substrate, the substrate heating temperature varied, etc.

TABLE 2

| Test No. | Substrate | Sample heating temperature | Substrate heating temperature | Reactant gas | Pressure | Deposition time |
|---|---|---|---|---|---|---|
| 1 | Si | 90° C. | 210° C. | Hydrogen 20 sccm | 150 torr | 180 min |
| 2 | SiO$_2$ | | | | | |
| 3 | Si | | 250° C. | | | 60 min |
| 4 | SiO$_2$ | | | | | |
| 5 | | | 350° C. | Hydrogen | 225 torr | 30 min |
| 6 | | 70° C. | 450° C. | 30 sccm | 150 torr | 40 min |

Figure 2:
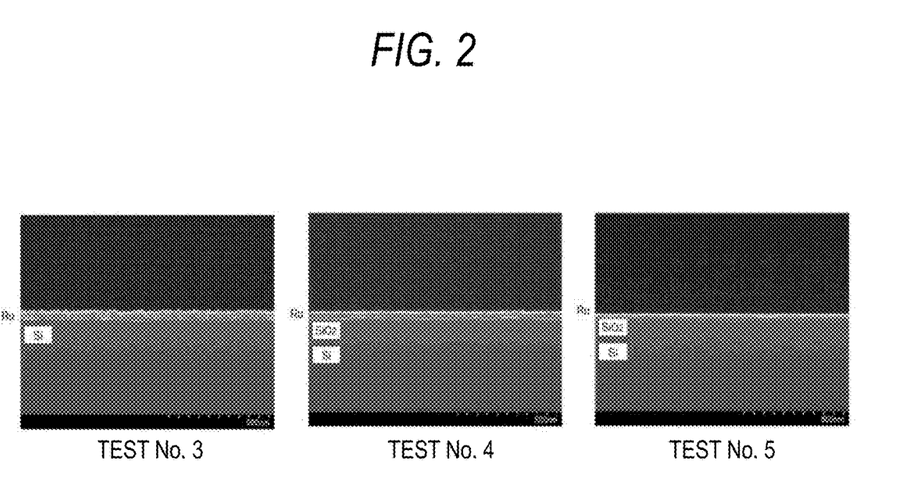
FIG. 2 shows SEM observation photographs of ruthenium thin films in this embodiment.

Film thickness measurement by SEM observation and specific resistance measurement were performed on the ruthenium films produced at the various substrate heating temperatures. FIG. 2 shows the SEM observation photographs of Test Nos. 3 to 5. Additionally, the specific resistance is shown in the following table.

TABLE 3

| Test No. | Substrate | Film thickness/nm | Specific resistance/μ Ω cm |
|---|---|---|---|
| 1 | SiO$_2$ | 46.3 | 59.1 |
| 2 | Si | 22.4 | 34.1 |
| 3 | SiO$_2$ | 30.3 | 16.8 |
| 4 | Si | 42.2 | 16.0 |
| 5 | SiO$_2$ | 8.5 | 28.4 |
| 6 | SiO$_2$ | 9.5 | 59.4 |

As a result of SEM observation, in all the ruthenium films produced at the above substrate heating temperatures, the thickness was uniform and continuous, and no cracks, holes, island-like aggregation, or the like was observed.

Additionally, with respect to the specific resistance, all the ruthenium films produced under the above test example conditions showed low specific resistances of 60 μΩcm or less. In particular, the ruthenium films of the Test Nos. 3 to 5, in which the substrate heating temperature at the time of deposition was 220° C. to 350° C., had particularly low specific resistances of 30 μΩcm or less.

INDUSTRIAL APPLICABILITY

The raw material according to the present invention has a high vapor pressure, moderate thermal stability, and also a low decomposition temperature (about 250° C. or less), offering excellent film formability at low temperatures, and its specific resistance is also low. Accordingly, the raw material is suitable also for use as a thin-film electrode material for a semiconductor device, such as DRAM or FERAM.

The invention claimed is:

1. A raw material for chemical deposition, for producing a ruthenium thin film or a ruthenium compound thin film by a chemical deposition method, the raw material for chemical deposition comprising an organoruthenium compound represented by the following formula, in which a derivative of a cyclohexadienyl group and a derivative of a pentadienyl group are coordinated to ruthenium, the organoruthenium compound having a decomposition temperature of 210° C. or more and 240° C. or less:

[Chemical Formula 1]

wherein the derivative of a cyclohexadienyl group is such that, out of the substituents $R_1$ to $R_7$, two to four substituents are each a hydrogen atom, and the remaining substituents are each a methyl group or an ethyl group, with the proviso that the substituents $R_6$ and $R_7$ are each a methyl group or an ethyl group, and the derivative of a pentadienyl group is dimethylpentadienyl wherein, out of the substituents $R_8$ to $R_{12}$, $R_8$, $R_{10}$, and $R_{12}$ are each a hydrogen atom, and the substituents $R_9$ and $R_{11}$ are each a methyl group.

2. A chemical deposition method for a ruthenium thin film or a ruthenium compound thin film, comprising the steps of:

vaporizing a raw material including an organoruthenium compound into a raw material gas; and heating and introducing the raw material gas onto a substrate surface, the chemical deposition method using the raw material for chemical deposition defined in claim 1 as the raw material, and heating the raw material gas at a temperature of 220° C. or more and 350° C. or less.

* * * * *